United States Patent

Lucey et al.

[11] Patent Number: 5,621,830
[45] Date of Patent: Apr. 15, 1997

[54] ROTATABLE FIBER OPTIC JOINT

[75] Inventors: Paul V. Lucey, Sandown; Roger D. Greeley, Portsmouth, both of N.H.

[73] Assignee: Smith & Nephew Dyonics Inc., Andover, Mass.

[21] Appl. No.: 475,900

[22] Filed: Jun. 7, 1995

[51] Int. Cl.$^6$ .................................................. G02B 23/26
[52] U.S. Cl. .............................................. 385/25; 385/118
[58] Field of Search .......................... 385/25, 26, 16–23, 385/117, 118

[56] References Cited

U.S. PATENT DOCUMENTS

| Re. 31,289 | 6/1983 | Moore et al. | 128/6 |
| Re. 31,290 | 6/1983 | Moore et al. | 128/6 |
| 4,253,447 | 3/1981 | Moore et al. | 128/6 |
| 4,261,344 | 4/1981 | Moore et al. | 128/6 |
| 4,273,109 | 6/1981 | Enderby | 128/6 |
| 4,294,511 | 10/1981 | Yamashita et al. | 350/96.18 |
| 4,401,365 | 8/1983 | Mizokawa et al. | 350/96.2 |
| 4,491,865 | 1/1985 | Danna et al. | 358/98 |
| 4,534,339 | 8/1985 | Collins et al. | 128/6 |
| 4,736,733 | 4/1988 | Adair | 128/6 |
| 4,854,302 | 8/1989 | Allred, III | 128/6 |
| 4,953,932 | 9/1990 | Mihich | 350/96.15 |
| 4,998,182 | 3/1991 | Krauter et al. | 361/394 |
| 5,222,477 | 6/1993 | Lia | 128/6 |
| 5,331,950 | 7/1994 | Wood, Sr. | 128/6 |
| 5,379,756 | 1/1995 | Pileski et al. | 128/6 |
| 5,438,638 | 8/1995 | Anderson | 385/20 |

FOREIGN PATENT DOCUMENTS

| 3840389A1 | 11/1988 | Germany | G02B 23/26 |
| 58-58509 | 4/1983 | Japan | 385/26 |
| 60-164707 | 8/1985 | Japan | 385/26 |
| 2030313 | 6/1978 | United Kingdom | G02B 23/02 |

Primary Examiner—John Ngo
Attorney, Agent, or Firm—Fish & Richardson P.C.

[57] ABSTRACT

An endoscope includes an insertion member rotatably mounted to a handle. A first set of optical fibers carried by the handle meets a second set of optical fibers disposed within the insertion member at a joint constructed to allow relative rotation between the sets of optical fibers about the longitudinal axis of the insertion member.

21 Claims, 4 Drawing Sheets

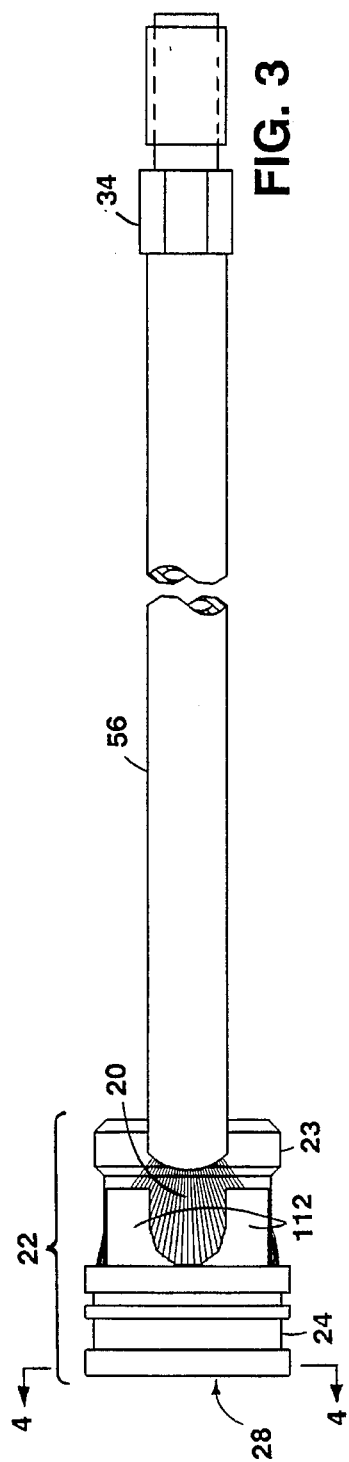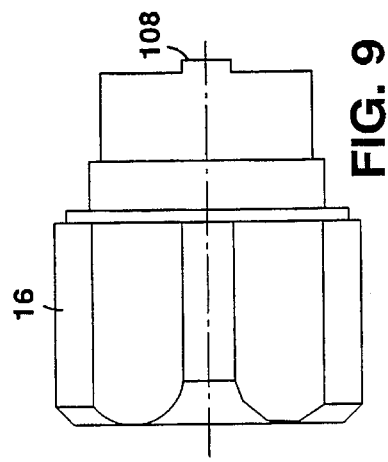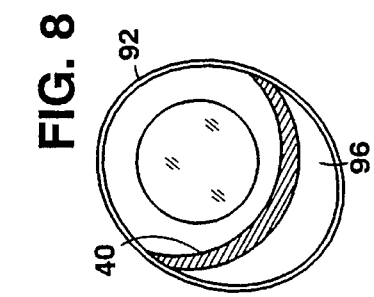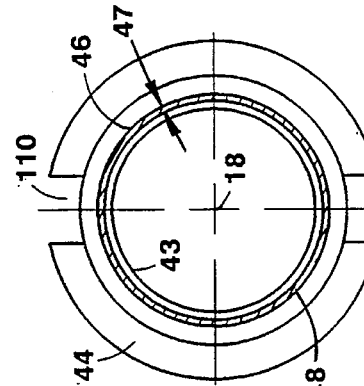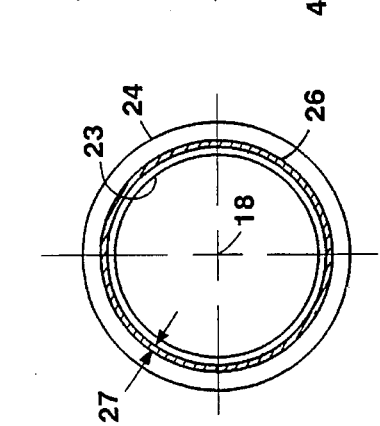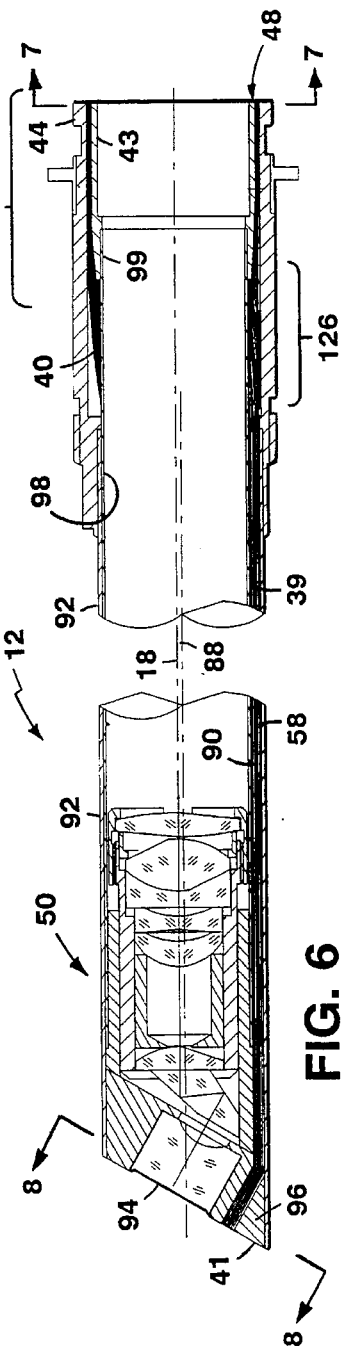

5,621,830

ROTATABLE FIBER OPTIC JOINT

BACKGROUND

This invention relates to endoscopes which use optical fibers to provide illumination.

Endoscopes are widely used to inspect regions of the body (e.g., joint spaces) through a small puncture wound. Typically, the endoscope includes an elongated insertion tube equipped with a set of optical fibers which extend from a proximal handle, through the insertion tube to the distal viewing tip of the endoscope. A cable that rigidly attaches to the handle (e.g., at a post on the side of the handle) carries light from an external light source to the proximal end of the optical fibers, and the light is transmitted through the optical fibers to the distal viewing end, where the light is emitted to illuminate the region under inspection.

Received light representing an optical image of the body region is collected by a lens assembly mounted in the distal viewing end and is passed to, e.g., a solid-state image pickup device (such as a charge-coupled-device, or CCD). The CCD converts the received optical image to electrical signals that are processed for viewing on a display.

Some endoscopes have a direction of view (i.e., the direction along which the endoscope emits and receives light) along the longitudinal axis of the insertion tube. The distal viewing ends of other endoscopes are constructed to provide an off-axis direction of view (e.g., at 30° or at 70°). The insertion tube of the latter type of endoscope is often rotatable with respect to the handle to allow the user to view different areas without requiring that the entire endoscope be rotated.

SUMMARY OF THE INVENTION

This invention features a rotatable joint between sets of optical fibers. The invention is particularly, but by no means exclusively, useful in an endoscope having an insertion tube rotatably mounted to the endoscope handle. In this case, one set of optical fibers is carried by the insertion tube, with another set of optical fibers being disposed in the handle.

The rotatable joint between the sets of optical fibers allows the insertion tube to be rotated (e.g., to change the viewing angle of the endoscope) without also rotating either the optical fibers in the handle or an external fiber optic cable that connects the handle to a light source. The fiber optic cable thus remains stationary and does not become twisted or wrapped around the handle when the insertion tube is rotated. The maneuverability of the endoscope is enhanced and the risk of damaging the fiber optic cable (and its associated connectors) is reduced substantially.

In one aspect of the invention, a portion of each of the first and second sets of optical fibers extends along a longitudinal axis, and the joint is constructed to allow relative rotation between the sets of optical fibers about the longitudinal axis.

Preferred embodiments include the following features.

The ends of the first and second sets of optical fibers are spring-biased together. This improves light transmission efficiency by reducing the spacing between the ends as much as possible.

Light transfer efficiency at the joint is further enhanced by a light transmitting substance, such as an immersion oil, placed between the ends of the respective sets of fibers. Preferably, the substance has an index of refraction substantially equal to that of at least one of sets of optical fibers. The substance also lubricates the joint. The joint is sealed to avoid leakage of the substance.

Another aspect of the invention features an endoscope, equipped with the rotatable joint.

Preferred embodiments include the following features. The endoscope includes an insertion member rotatably mounted to a handle. The handle and insertion member carry the first and second set of optical fibers, respectively. Individual fibers of the first and second sets of optical fibers are arranged in first and second annular rings, respectively. These annular rings are adjacent to one another, are centered about the longitudinal axis, and are spring-biased together. The width of the first annular ring is greater than the width of the second annular ring, thereby maintaining efficient light transfer even if the rings become misaligned.

The endoscope also includes an optical element and an image detector mounted in the distal end of the insertion tube. Preferably, the optical element (which includes at least one lens) is configured to provide a direction of view at a nonzero angle with respect to the longitudinal axis. The image detector is a solid-state image pickup device, such as a CCD.

Other features and advantages of the invention will become apparent from the following detailed description, and from the claims.

BRIEF DESCRIPTION OF THE DRAWINGS

FIG. 3 shows one of the components of the rotatable joint in detail.

FIG. 4 is a cross-section of a portion of the component of FIG. 3, taken along line 4—4.

FIG. 6 is an enlarged cross-sectional view of the insertion tube of the endoscope of FIG. 1 and of another component of the rotatable joint.

FIG. 7 is a cross-section of a portion of the component of FIG. 6, taken along line 7—7.

FIG. 8 is a cross-section, taken along line 8—8 of FIG. 6, showing the distal viewing tip of the endoscope.

FIG. 9 illustrates the actuator of the rotatable joint.

DESCRIPTION OF A PREFERRED EMBODIMENT

Figure 1:
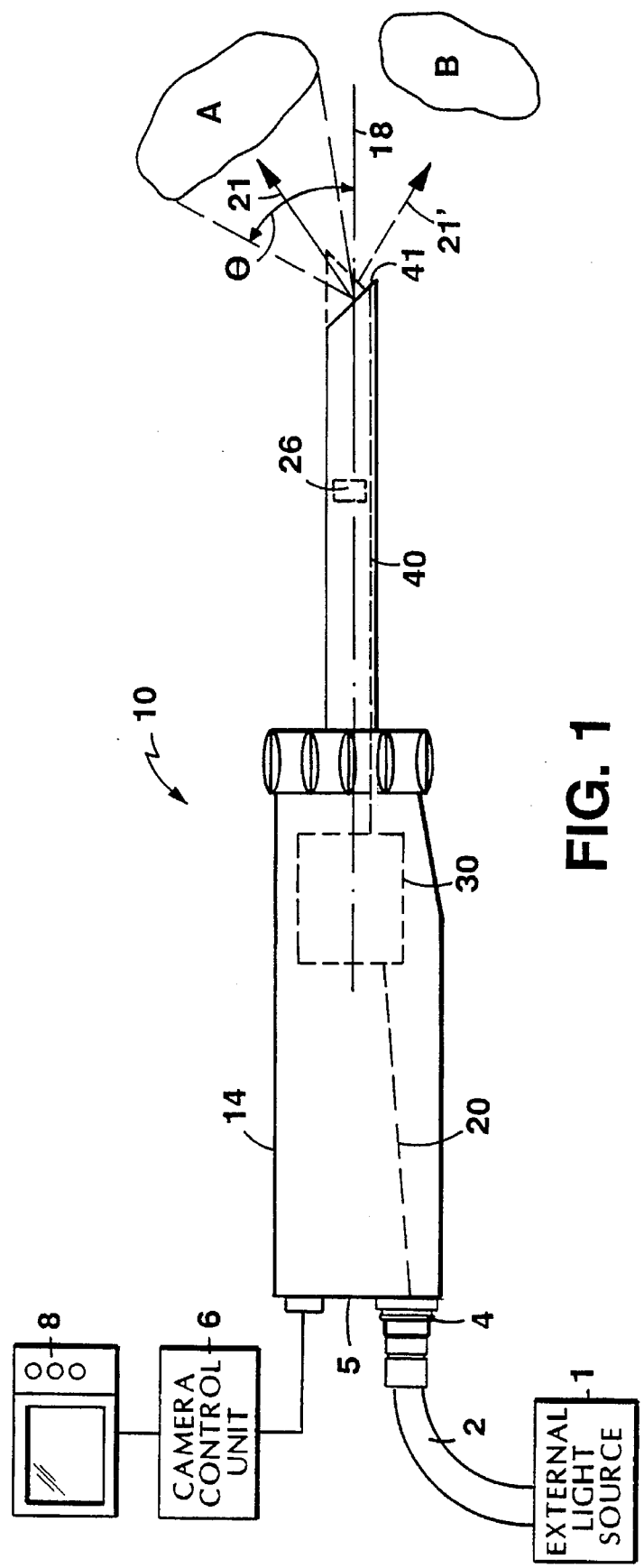
FIG. 1 is a diagrammatic view of an endoscope equipped with a rotatable joint between sets of optical fibers in the handle and in the insertion tube of the endoscope.

Referring to FIG. 1, endoscope 10, suitable for viewing into a body cavity, joint space, or passageway during arthroscopic surgery, includes an elongated insertion tube 12 rotatably mounted to handle 14. Actuator 16, which is also rotatably mounted to handle 14, is manipulated by a user to rotate insertion tube 12 about a longitudinal axis 18 to rotatably orient insertion tube 12 with respect to an area to be viewed, e.g., area A or area B.

External light source 1 provides the light used to illuminate areas A and B via a light cable connected to a proximal surface 5 of handle 14 at coupler 4. A first set 20 of optical fibers, extending through handle 14 from light coupler 4 to joint 30 (shown schematically), transmits light received from source 1 to a second set 40 of optical fibers, which meet optical fiber set 20 at joint 30. The optical fibers in set 40 extend from joint 30 through insertion tube 12 to distal viewing tip 41, to transmit light out distal viewing tip 41 to area A or area B.

The construction and operation of joint 30 are described in detail below. Suffice it here to say that joint 30 enables relative rotation between optical fiber sets 20, 40 about axis 18 when insertion member 12 is rotated with respect to handle 14 by actuator 16, while also providing efficient light transmission between them.

Endoscope 10 has an off-axis direction of view, i.e., a direction of view oriented at a nonzero angle with respect to longitudinal axis 18. The direction of view is determined by the orientation of a lens assembly 50 (FIG. 2) at distal viewing tip 41 (i.e., the angle formed between longitudinal axis 18 and a vector 21 that is perpendicular to the lens at distal viewing tip 41) and is typically 30°, 45°, or 70°. The field of view, angle Θ, is an angle within which the endoscope receives light from external objects, i.e., the angle over which the endoscope "sees," and is equidistant on either side of vector 21.

Endoscope 10 illuminates (and views, as described below) area A when insertion tube is oriented as shown in FIG. 1. To illuminate and view another area, e.g., area B, a user rotates actuator 16, which rotates insertion tube 12 with respect to handle 14 about longitudinal axis 18, to orient distal viewing tip 41 to view area B along vector 21' (shown in dashed lines). Rotatable joint 30 allows set 20 of optical fibers and external cable 2 to remain stationary when insertion tube 12 is rotated. As a result, cable 2 does not become twisted or wound about handle 14 when insertion tube is rotated. This makes endoscope 10 easier to use and manipulate in the body. Moreover, the stresses imposed on optical fiber set 20 and cable 2 are significantly reduced, particularly at light coupler 4, which increases reliability and operating lifetime.

Figure 2:
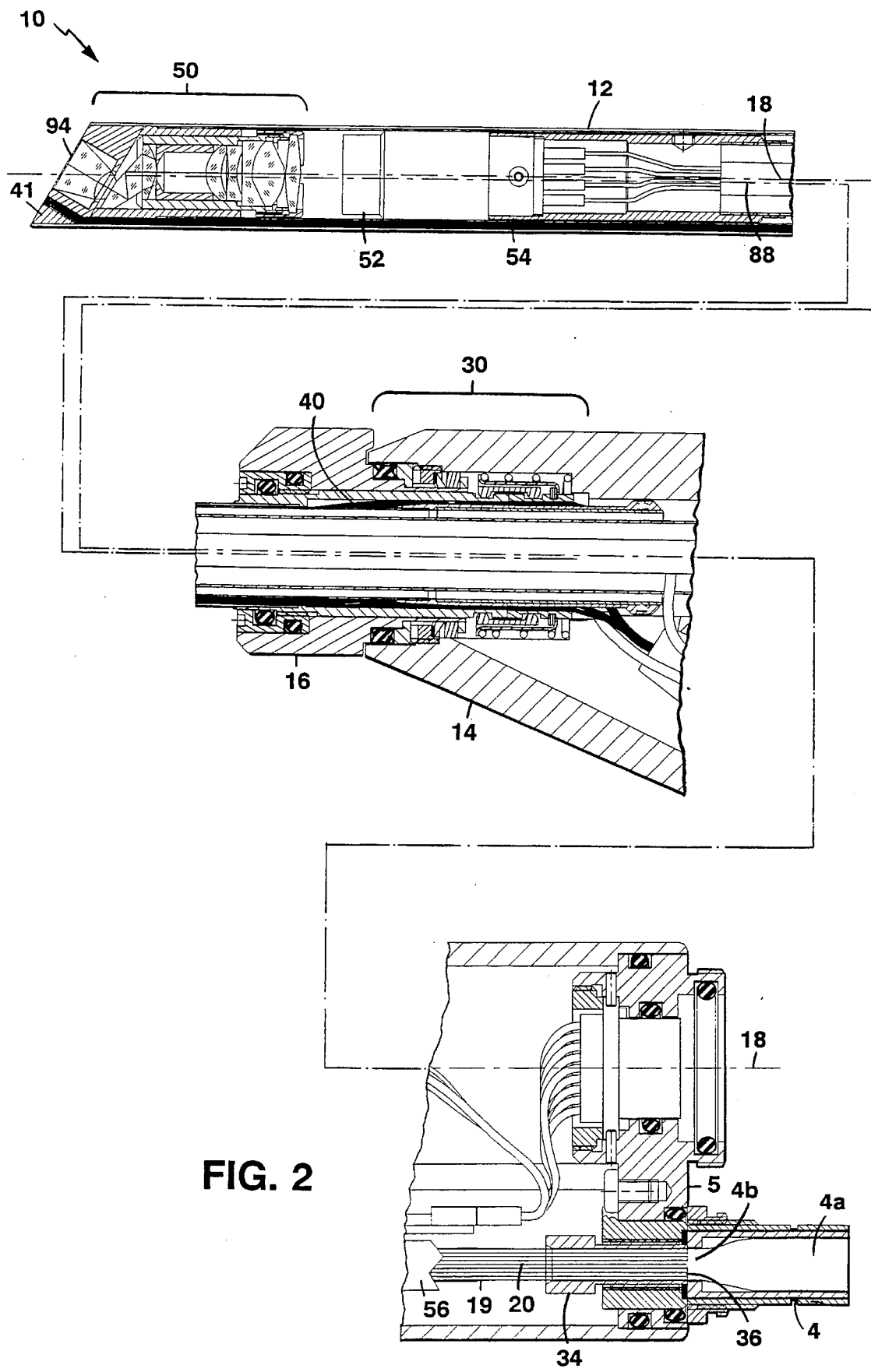
FIG. 2 is a cross-sectional view of the endoscope of FIG. 1.

Referring to FIG. 2, light from objects illuminated by endoscope 10 is collected by lens assembly 50 mounted in distal viewing tip and passed to a charge-coupled-device (CCD) 52 or other suitable image detector supported proximally to lens assembly 50 at the distal end of a CCD tube 54. CCD 52 converts the light into electrical signals representing an image of the objects. The electrical signals are transmitted (by wiring which extends through CCD tube 54 and through handle 14) to a camera control unit 6 for processing in the usual manner. The resultant image is displayed on display screen 8 (FIG. 1).

CCD 52, including its associated electrical and optical systems, are of the type described in detail in copending U.S. patent application Ser. No. 07/958,688, filed Oct. 9, 1992, incorporated herein by reference. In particular, as described in the '668 application, upon manipulation of a focusing mechanism by a user, CCD tube 54 and CCD 52 are moved axially along longitudinal axis 18 with respect to lens assembly 50. This motion changes the spacing between lens assembly 50 and CCD 52, thereby adjusting the focus of the image.

Referring also to FIGS. 3–6, rotatable joint 30 will be described in detail. At joint 30, the individual optical fibers of sets 20, 40 are arranged in a pair of annular fiber rings 26, 46, each of which surrounds CCD tube 54, is centered about longitudinal axis 18, and extends for a short distance along longitudinal axis 18. Annular fiber rings 26, 46 abut each other at joint 30 for efficient light transmission therebetween, and are mounted within handle 14 for relative rotation, as will be described.

FIGS. 3 and 4 show the construction of set 20 of optical fibers and a stationary annulus 22 that defines annular fiber ring 26. Sheath 56 carries optical fiber set 20 from light coupler 4 to joint 30. At joint 30, the distal ends of individual glass fibers 19 of set 20 are removed from sheath 56 and are arranged evenly around the exterior surface of an inner ring 23. A slightly larger, outer ring 24 surrounds inner ring 23 and captures fibers 19 therebetween. Inner and outer rings 23, 24 each extend along longitudinal axis 18 and are sized such that individual optical fibers 19 are densely arranged between inner ring 23 and outer ring 24. Fibers 19 are epoxied in place between rings 23, 24 and are cut off at the face 28 of rings 23, 24. The ends of optical fibers 19 are polished flat to form annular fiber ring 26.

Referring as well to FIGS. 6–7, annular fiber ring 46 likewise is formed by securing the proximal ends of individual optical fibers 39 of set 40 between an elongated inner ring 43 and an elongated outer ring 44, which together form a rotatable annulus 42. Optical fibers 39 are arranged evenly around the exterior of ring 43, and are surrounded by outer ring 44 to form annular ring 46 of optical fibers at a face 48 of rings 43, 44. Inner and outer rings 43, 44 are sized such that individual optical fibers 39 are densely arranged therebetween for maximum light transfer. Individual optical fibers 39 of optical fibers 40 are secured between inner and outer rings 43, 44 by, for example, an epoxy, and are also arranged such that at ring face 48, the individual optical fibers are parallel to longitudinal axis 18 and are polished flat at the ends, for efficient light transmission.

Individual fibers 39 extend from the distal end of rotating annulus 42 and are gathered within a channel 58 in insertion tube 12. Channel 58 carries optical fibers 39 from joint 30 to distal viewing tip 41.

Referring in particular to FIGS. 4 and 7, annular fiber rings 26, 46 are each centered about longitudinal axis 18 and are in radial alignment. The radial thickness 27 of annular fiber ring 26 is, however, greater than the radial thickness 47 of annular fiber ring 46. For example, radial thickness 27 is 0.3 mm, while radial thickness 47 is 0.2 mm (and as a result, fiber ring 26 extends 0.05 mm radially inwardly and outwardly of fiber ring 46). (The individual optical fibers 19, 39 are each about 2.0 mil in diameter.)

Figure 5:
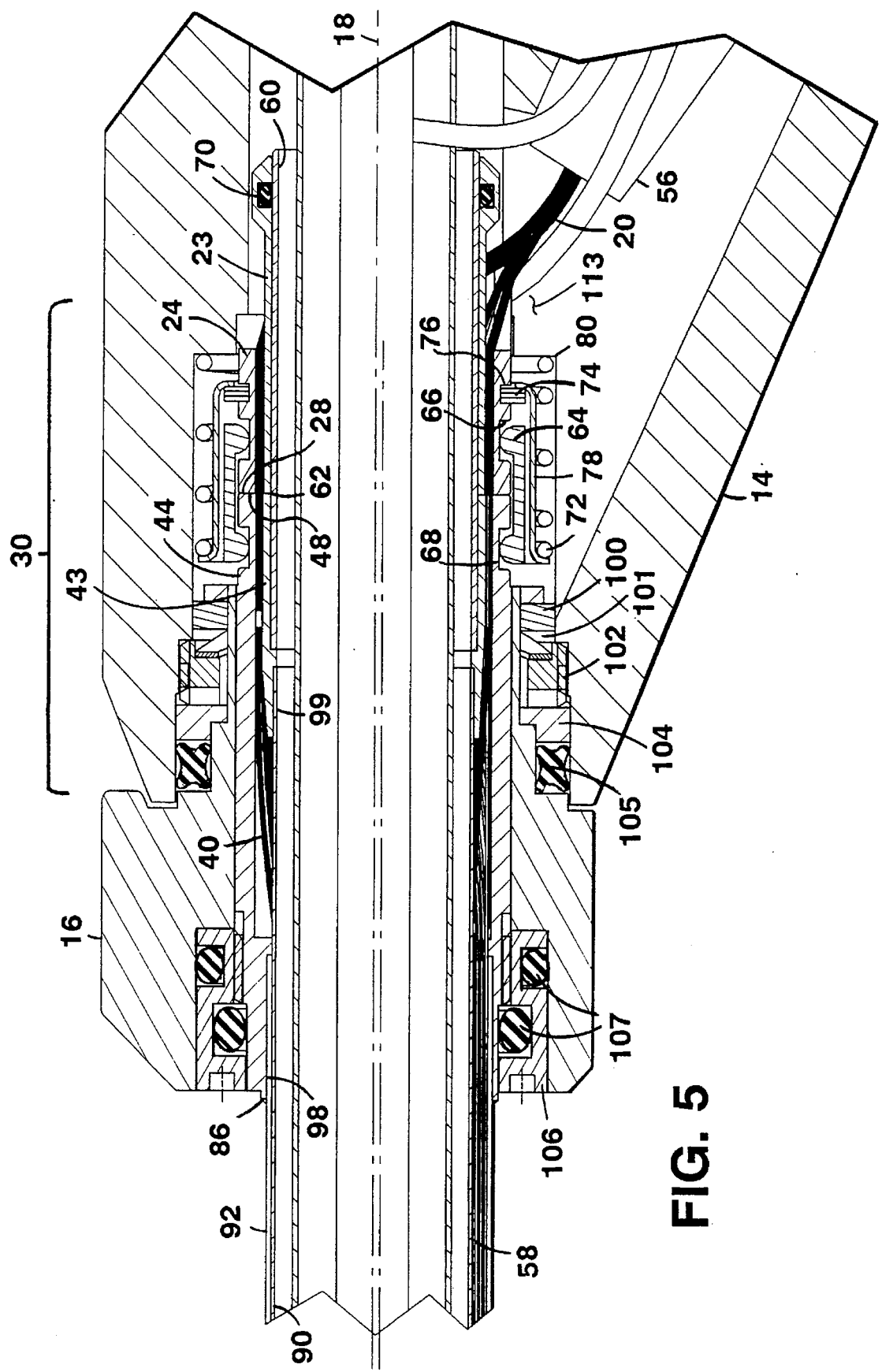
FIG. 5 is an enlarged cross-sectional view of the rotatable joint.

Referring to FIG. 5, annuli 22, 42 are each disposed over a sleeve 60 within handle 14 (CCD tube 54 passes through sleeve 60) so that faces 28, 48 (and hence fiber rings 26, 46) abut each other. Sleeve 60 is bonded to rotating annulus inner ring 43 by a retaining compound, such as, for example, Loctite 620. Sleeve 60 centers annular fiber rings 26, 46 with respect to longitudinal axis. The radial overlap between fiber rings 26, 46 discussed above helps ensure efficient light transfer between fibers 19, 39, even if annular fiber rings 26, 46 are slightly radially misaligned.

Outer ring 44 of rotating annulus 42 is secured to actuator 16 in a manner described in detail below. When actuator 16 is rotated, it causes annulus 42 and sleeve 60 to rotate with respect to annulus 22 (which is held stationary within handle 14 by the engagement of anti-rotation tabs 112 (FIG. 3) on ring 24 within a corresponding throat 113 in handle 14). To enhance light transmission between the abutting fiber rings 26, 46, a light transmissive fluid 62 (such as immersion oil, e.g., type A manufactured by Cargille Labs) is disposed between faces 28, 48 over sleeve 60. Fluid 62 has index of refraction substantially equal to that of one, or preferably both, sets 20, 40 of optical fibers 20, 40. In addition, fluid 62 lubricates joint 30 for ease of use.

A seal 64, preferably made from rubber, retains fluid 62 within joint 30 between faces 28, 48. Seal 64 is sized to securely fit over the abutting portions of outer rings 24, 44. The proximal and distal ends of seal 64 are enlarged and snugly disposed in corresponding grooves 66, 68 machined in outer rings 24, 44, respectively. 0-ring 70 provides a seal between stationary annulus inner ring 23 and sleeve 60 to prevent fluid 62 from leaking from the proximal end of joint 30 into handle 14.

Stationary annulus 22 is biased toward rotating annulus 42 by coil spring 72, which exerts approximately a one pound force, to urge stationary ring face 28 against rotating ring face 48. This further improves light transfer by reducing the gap between fiber rings 26, 46 to as small as possible. One end of spring 72 abuts an inner wall 80 of handle 14. The other end of spring 72 engages one end of a cylindrical spring retainer 78. The opposite (proximal) end of spring retainer engages a retaining ring 74 secured within a groove 76 machined in outer ring 24. Thus, retaining ring 74 acts as a flange surface for spring retainer 78. (A discrete retaining ring 74 is used instead of an integral flange because during manufacturing it is necessary to grip stationary annulus 22 to polish the ends of the individual optical fibers 19 at ring face 28; an integral flange would make this manufacturing step more difficult.)

Cylindrical spring retainer 78 surrounds seal 64 and the abutting faces 28, 48 of annuli 22, 42. The force of spring 72 urges spring retainer 78 distally away from wall 80, thereby biasing stationary annulus 22 (via retaining ring 74) against rotating annulus 42.

Referring to FIGS. 2, 6, and 8, insertion tube 12 includes inner tube 90 and outer tube 92 (CCD tube 54 is disposed within inner tube 90). Inner tube 90 and outer tube 92 are aligned along different axes—longitudinal axis 18 and longitudinal axis 88, respectively. The offset between longitudinal axis 18 and longitudinal axis 88, which is preferably about 0.013 inches, creates the above-described channel 58 between inner tube 92 and outer tube 90 for optical fibers 40. CCD tube 54, CCD 52, and lens assembly 50 are aligned along longitudinal axis 18.

At distal viewing tip 41, window lens 94 of lens assembly 50 is oriented with respect to longitudinal axis 18 to determine the direction of view of endoscope 10 and could be recessed from the distal end of outer tube 92 to protect its exposed distal surface. Wedge 96, at distal viewing tip 41, deflects optical fibers 40 such that light is directed along the direction of view in accordance with the orientation of window lens 94, e.g., at 30° with respect to axis 18. As shown in FIG. 8, individual optical fibers 39 of optical fibers 40 are arranged in a crescent shape, corresponding to the shape of channel 58 formed between inner tube 90 and outer tube 92, to disperse the light across the width of insertion tube 12.

Lens assembly 50, wedge 96, and optical fibers 40 are all bonded within the distal end of outer tube 92 by, for example, an epoxy. Lens assembly 50 is also epoxied to the distal end of inner tube 90. CCD tube 54 is axially movable within inner tube 90 for focussing, as discussed above.

The proximal end of outer tube 92 is inserted into an eccentric bore 98, aligned about longitudinal axis 88, within the distal end of rotating annulus outer ring 44. Outer tube 92 is attached to the distal end of outer ring 44 by, for example, weld 86. Inner tube 90 is attached to inner wall 99 of rotating annulus inner ring 43, by, for example, an epoxy. Actuator 16 is inserted onto the distal end of handle 14 over tubes 90, 92. Thrust washer 100, wave spring 101, threaded retainer 102, and thrust washer 104 are radially mounted over the proximal end of actuator 16. Thrust washers 100, 104 provide radial bearings and are preferably made from a plastic having exceptional bearing characteristics, such as, for example, Torlon 4301.

Retainer 106, threaded into rotating annulus outer ring 44, holds tubes 90, 92 (and the components of joint 30) and actuator 16, respectively, within handle 14. Seal 105, preferably a quad ring, seals the interface between actuator 16 and handle 14. Seals 107 avoid contaminants from entering handle 14 at the interface between actuator 16 and ring 43.

Referring as well to FIG. 9, the proximal end of actuator 16 includes tabs 108 (only one of which is shown) which engage corresponding slots 110 (FIG. 7) formed in rotating annulus outer ring 44. Accordingly, when actuator 16 is rotated, tabs 108 engage slots 110 to rotate annulus outer ring 44, thereby also rotating inner ring 43, optical fibers 40, and tubes 90, 92 (which are attached to inner and outer rings 43, 44, respectively) about longitudinal axis 18. Anti-rotation tabs 112 (see FIG. 3) on stationary annulus outer ring 24 engage throat 113 in handle 14 to prevent the frictional forces between stationary annulus 22 and rotating annulus 44 to cause stationary annulus 22 to rotate. CCD tube 54, which is coupled to handle 14 at the focusing mechanism (not shown), including CCD 52 and its associated electrical and optical systems, also remains stationary.

FIG. 2 shows the connection between external fiber optic cable 2 (FIG. 1) and optical fiber set 20 at the proximal end 5 of handle 14. The individual fibers 19 of set 20 are epoxied into threaded bushing 34, and the proximal ends 36 of optical fibers 29 are uniformly polished for efficiently receiving light from light coupler 4. Light coupler 4 is designed to change the numerical aperture of light cable 2, which has a relatively low value (e.g., 0.54) for efficient light transfer, to a higher value (e.g., 0.81), which is desirable for adequately illuminating area A (FIG. 1). This is done by providing light coupler 4 with different inside diameters 4a, 4b at its ends. That is, diameter 4a is relatively large (5¼ mm) where cable enters coupler 4, and is reduced substantially (to a diameter, 4b, of 3½ mm) at the junction between cable 2 and optical fiber set 28. The ratio between diameters 4a and 4b multiplied by the numerical aperture of cable 2 (0.54) provides the desired numerical aperture (0.81) of optical fiber set 28.

In use, insertion tube 12 of endoscope 10 is inserted into a body cavity, joint space, or passageway during arthroscopic surgery. Distal viewing tip 41 is oriented such that the desired area (e.g., area A, FIG. 1) within the body cavity is within the field of view of endoscope 10 and is illuminated by light emitted from optical fibers 39 at distal viewing tip 41. Light from objects in field of view is collected by lens assembly 50 and passed to CCD 52. CCD 52 converts the received optical image to electrical signals, which are processed by CCU 6 to display an image of the objects on display screen 8.

To view a different area (such as area B), the user rotates actuator 16 while holding handle 14 stationary. As discussed, the rotation of actuator 16 causes tubes 90, 92, and hence also lens assembly 50, to rotate about longitudinal axis. In addition, actuator 16 rotates annulus 42—and hence annular fiber ring 46—with respect to annulus 22 and annular fiber ring 26. The rotation is not conveyed to either set 20 of optical fibers or external light cable 2.

Other embodiments are within the scope of the following claims.

For example, inner tube 90 and outer tube 92 may be coaxial so that the channel created for optical fibers 39 is annular. Likewise, other arrangements of individual optical fibers 39 at distal viewing tip 41 can be used. For example, optical fibers 99 can be arranged in an annular ring about the perimeter of window lens 94.

Other features may be added to the endoscope. For example, focussing capability may be provided, as described in the aforementioned '668 patent application. In addition, the endoscope can include the CCD rotation feature described in a patent application entitled "Endoscope" filed concurrently herewith, assigned to the present assignee, and incorporated herein by reference.

What is claimed is:

1. An apparatus for viewing a remote region, comprising:

a handle;

an elongated outer member configured to be inserted into the remote region and having a proximal end rotatably mounted to said handle;

a device disposed in a distal end of said outer member for viewing the remote region, a portion of said device being coupled to said handle by an inner member disposed along an axis within said outer member;

a first set of optical fibers disposed in said handle and having a distal end at which individual fibers thereof are arranged around said inner member;

a second set of optical fibers disposed in said outer member and having a proximal end at which individual fibers thereof are arranged around said inner member; and a joint between said distal end of said first set of optical fibers and said proximal end of said second set of optical fibers, said inner member extending through said joint, said joint being constructed to allow relative rotation between said first and second sets of optical fibers about said axis of said inner member in response to relative rotation between said outer member and said handle.

2. The apparatus of claim 1 wherein said joint is constructed to maintain said distal end of said first set of optical fibers and said proximal end of said second set of optical fibers adjacent to one another for light transmission therebetween.

3. An apparatus for viewing a remote region, comprising:

a handle;

an elongated outer member configured to be inserted into the remote region and having a proximal end rotatably mounted to said handle;

a device disposed in a distal end of said outer member for viewing the remote region, a portion of said device being coupled to said handle by an inner member disposed along an axis within said outer member;

a first set of optical fibers disposed in said handle and having a distal end at which individual fibers thereof are arranged around said inner member;

a second set of optical fibers disposed in said outer member and having a proximal end at which individual fibers thereof are arranged around said inner member;

a joint between said distal end of said first set of optical fibers and said proximal end of said second set of optical fibers, said inner member extending through said joint, said joint being constructed to allow relative rotation between said first and second sets of optical fibers about said axis of said inner member in response to relative rotation between said outer member and said handle; and a spring mounted to bias said distal end of said first set of optical fibers and said proximal end of said second set of optical fibers together to maintain said ends of said first and second sets of optical fibers adjacent to one another for light transmission therebetween.

4. The apparatus of claim 3 further comprising a light-transmitting substance disposed between said distal end of said first set of optical fibers and said proximal end of said second set of optical fibers.

5. An apparatus comprising:

a first set of optical fibers having at least a portion extending along a longitudinal axis;

a second set of optical fibers having at least a portion extending along said longitudinal axis;

a joint between an end of said portion of said first set of optical fibers and an end of said portion of said second set of optical fibers constructed to allow relative rotation between said portions about said longitudinal axis;

a spring mounted to bias said ends of said portions of said first set of optical fibers and said second set of optical fibers together to maintain said ends adjacent to one another for light transmission therebetween; and a light-transmitting substance disposed between said ends of said portions of said first set of optical fibers and said second set of optical fibers, said substance having an index of refraction substantially equal to an index of refraction of at least one of said first and said second sets of optical fibers.

6. An apparatus comprising:

a first set of optical fibers having at least a portion extending along a longitudinal axis;

a second set of optical fibers having at least a portion extending along said longitudinal axis;

a joint between an end of said portion of said first set of optical fibers and an end of said portion of said second set of optical fibers constructed to allow relative rotation between said portions about said longitudinal axis;

a spring mounted to bias said ends of said portions of said first set of optical fibers and said second set of optical fibers together to maintain said ends adjacent to one another for light transmission therebetween; and immersion oil disposed between said ends of said portions of said first set of optical fibers and said second set of optical fibers.

7. The apparatus of claim 5 wherein said substance is a liquid and said joint is constructed to contain said liquid between said ends of said portions of said first and said second sets of optical fibers.

8. An apparatus for delivering light from a source to a region remote from the source and viewing the region, comprising:

a handle;

an elongated outer member having a proximal end rotatably mounted to said handle, said outer member configured to be inserted into the remote region;

a device disposed in a distal end of said outer member for viewing the remote region, a portion of said device being coupled to said handle by an inner member disposed along an axis within said outer member;

a first set of optical fibers carried within said handle and having a proximal end configured to receive light from the source and a distal end at which individual fibers thereof are arranged around said inner member; and a second set of optical fibers carried within said outer member and having a proximal end and a distal end, said distal end of said second set of optical fibers being configured to transmit light from said outer member into said remote region, individual fibers of said second set of optical fibers being arranged around said inner members at said proximal end of said second set of fibers; and said outer member being rotatably mounted to said handle at a joint between said distal end of said first set of optical fibers and said proximal end of said second set of optical fibers, said inner member extending through said joint, said joint being constructed to allow relative rotation between said first and second sets of optical fibers about said axis of said inner member in response to relative rotation between said outer member and said handle.

9. An apparatus for delivering light from a source to a region remote from the source and viewing the region, comprising:

a handle;

an elongated outer member having a proximal end rotatably mounted to said handle, said outer member configured to be inserted into the remote region;

a device disposed in a distal end of said outer member, a portion of said device being coupled to said handle by an inner member disposed along a longitudinal axis within said outer member;

a first set of optical fibers carried within said handle and having a proximal end and a distal end, said proximal end being configured to receive light from the source, said distal end of said first set of optical fibers being configured so that individual fibers thereof are arranged in a first annular ring around said inner member;

a second set of optical fibers carried within outer member, said second set of optical fibers having a proximal end and a distal end, said distal end configured to transmit light from said outer member into said remote region, said proximal end of said second set of optical fibers being configured so that individual fibers thereof are arranged in a second annular ring around said inner member;

said outer member being rotatably mounted to said handle at a joint, said inner member extending through said joint, said joint being constructed to position said first and said second annular rings adjacent to one another and centered about said longitudinal axis and to allow relative rotation between said first and second sets of optical fibers about said longitudinal axis of said inner member in response to relative rotation between said outer member and said handle.

10. The apparatus of claim 9 wherein said first annular ring is configured with a width greater than a width of said second annular ring.

11. The apparatus of claim 9 further comprising a substance disposed between said first annular ring and said second annular ring, said joint being constructed to contain said substance between said first and said second annular rings.

12. The apparatus of claim 9 wherein said joint includes a spring to bias said first annular ring and said second annular ring together.

13. An endoscope comprising:

a handle that carries a first set of optical fibers having a proximal end and a distal end, said proximal end being configured to receive light from a light source, an elongated outer member configured to be inserted into a remote region and rotatably mounted to said handle, said outer member carrying a second set of optical fibers having a proximal end and a distal end configured to transmit light from said distal end of said outer member to the remote region, a device disposed at said distal end of said outer member for viewing the remote region, said device including an optical element and an image detector disposed adjacent to said optical element, said image detector being coupled to said handle by an inner member disposed along an axis within said outer member, said distal end of said first set of optical fibers including a first ring of individual fibers arranged around said inner member, said proximal end of said second set of optical fibers including a second ring of individual fibers arranged around said inner member, said first ring of optical fibers and said second ring of optical fibers being disposed adjacent to each other at a rotatable joint between said outer member and said handle, said inner member extending through said joint, said joint being constructed to allow relative rotation between said first and second sets of optical fibers about said axis of said inner member in response to relative rotation between said outer member and said handle.

14. The endoscope of claim 13 wherein said optical element is configured to provide a direction of view at a nonzero angle with respect to said longitudinal axis.

15. The endoscope of claim 13 wherein said optical element includes at least one lens.

16. The endoscope of claim 13 wherein said image detector is a solid-state image pickup device.

17. The apparatus of claim 1 wherein said individual fibers at said distal end of said first set of optical fibers are symmetrically arranged about said axis, and said individual fibers at said proximal end of said second set of optical fibers are symmetrically arranged about said axis.

18. The apparatus of claim 1 wherein said individual fibers of said distal end of said first set of optical fibers are arranged in an annular ring about said axis, and said individual fibers of said proximal end of said second set of optical fibers are arranged in an annular ring about said axis.

19. The apparatus of claim 8 wherein said individual fibers at said distal end of said first set of optical fibers are symmetrically arranged about said axis, and said individual fibers at said proximal end of said second set of optical fibers are symmetrically arranged about said axis.

20. The apparatus of claim 8 wherein said individual fibers of said distal end of said first set of optical fibers are arranged in an annular ring about said axis, and said individual fibers of said proximal end of said second set of optical fibers are arranged in an annular ring about said axis.

21. An endoscope comprising:

a handle that carries a first set of optical fibers having a distal end;

an elongated outer member rotatably mounted to said handle, said outer member being configured to be inserted into a body and carrying a second set of optical fibers having a proximal end;

a device disposed in a distal end of said outer member for viewing the body, a portion of said device being coupled to said handle by an inner member disposed along an axis within said outer member, individual fibers at said distal end of said first set of optical fibers being arranged around said inner member, individual fibers at said proximal end of said second set of optical fibers being arranged around said inner member; and a joint between said distal end of said first set of optical fibers and said proximal end of said second set of optical fibers, said inner member extending through said joint, said joint being constructed to allow relative rotation between said first and second sets of optical fibers about said axis of said inner member in response to relative rotation between said outer member and said handle.

* * * * *